| United States Patent [19] | [11] Patent Number: 4,782,136 |
| Goldberg et al. | [45] Date of Patent: Nov. 1, 1988 |

[54] SYNTHETIC PEPTIDE COMPOUNDS PRODUCING ANITBODIES BINDING TO HUMAN LDH-C$_4$

[75] Inventors: Erwin Goldberg, Evanston, Ill.; Jose L. Millan, San Diego, Calif.

[73] Assignee: Northwestern University, Evanston, Ill.

[21] Appl. No.: 936,170

[22] Filed: Dec. 1, 1986

[51] Int. Cl.$^4$ .......................... C07K 7/08; C07K 7/06; C07K 7/10

[52] U.S. Cl. ................................. 530/326; 530/327; 530/329

[58] Field of Search ........................ 530/329, 327, 326

[56] References Cited

U.S. PATENT DOCUMENTS

| | | | |
|---|---|---|---|
| 4,290,944 | 9/1981 | Goldberg | 260/112.5 R |
| 4,354,967 | 10/1982 | Goldberg | 260/112.5 R |
| 4,392,997 | 7/1983 | Goldberg | 260/112.5 R |
| 4,578,219 | 3/1986 | Goldberg et al. | 530/327 |
| 4,585,587 | 4/1986 | Goldberg et al. | 530/329 |

OTHER PUBLICATIONS

Beyler et al, Biology of Reproduction, vol. 32, pp. 1201–1210 (1985).
Wheat et al, Molecular Immunology, vol. 22 No. 10, pp. 1195–1199 (1985).
Ibarra et al, Chem. Abstr., vol. 103 No. 352276 (1985) (Abstract of Arch Invest. Med. 15(3) 239–244, 1984).
Goldberg et al, Chem. Abstr., vol. 105 No. 203204d (1986).
Beyler et al, Chem. Abstr., vol. 103 No. 116459f (1985) Abstract of Biol. Reprod. 32(5) 1201–1210, 1985.
Goldberg and Shelton, Chapt. 42, pp. 435–446 in Zatuchni, et al. (Eds.), "Male Contraception", (Harper & Row, Philadelphia, 1986).
Pan et al. (1983), J. Biol. Chem. 258:7005–7016.
Li et al. (1983), J. Biol. Chem. 258:7017–7028.
Goldberg et al. (1983), In Immunology of Reproduction, Chapt. 22, pp. 493–504.
Wheat and Goldberg (1983), In Isozymes: Current Topices in Biological and Medical Research, vol. 7, pp. 113–140.
Wheat and Goldberg (1985), Mol. Immunol. 22:643–649.

*Primary Examiner*—J. R. Brown
*Assistant Examiner*—Christina Chan
*Attorney, Agent, or Firm*—Tilton, Fallon, Lungmus & Chestnut

[57] ABSTRACT

Synthetic peptide compounds are provided which are capable of producing antibodies binding to the lactate dehydrogenase enzyme of human serum (LDH-C$_4$). The peptide compounds comprise antigenic sequences of human LDH-C$_4$. The peptide compounds can be used to prepare vaccines for reducing the fertility of women.

7 Claims, No Drawings

SYNTHETIC PEPTIDE COMPOUNDS PRODUCING ANITBODIES BINDING TO HUMAN LDH-C$_4$

GRANT REFERENCE

This invention was developed in part under Grant HD 05863 by the National Institutes of Health.

FIELD OF INVENTION

The field of this invention is synthetic peptide compounds capable of producing antibodies to the lactate dehydrogenase enzyme of mammalian semen (LDH-C$_4$). Such peptides can be used to prepare vaccines for reducing fertility of females.

BACKGROUND OF INVENTION

Mammalian spermatozoa have been known to be antigenic for many years. More recently, it has been demonstrated that mammalian sperm contain an antigenic enzyme, which is known as the C$_4$ isoenzyme of lactate dehydrogenase (LDH-C$_4$) LDH-C$_4$ has been isolated in pure crystalline form from mouse testes. Goldberg (1972), *J. Biol. Chem.* 247:2044-2048. The enzyme has a molecular weight of 140,000 and is composed of four identical C subunits. The amino acid sequence and three-dimensional structure of mouse LDH-C$_4$ have been studied-described by a number of investigators: Musick, et al. (1976), *J. Mol. Biol.* 104:659-668; Wheat, et al. (1977), *Biochem. & Biophys. Res. Comm.* 74, No. 3:1066-1077; Li et al. (1983), *J. Biol. Chem.* 258:7017-7028; and Pan, et al. (1983), *J. Biol. Chem.* 258:7005-7016.

In 1974, Dr. Erwin Goldberg reviewed the effects of immunization with LDH-X (LDH-C$_4$) on fertility, and advanced the possibility that "by using a defined macromolecular constituent of sperm it becomes possible to elucidate its primary structure in terms of amino acid sequence, to map specifically the antigenic determinant(s) responsible for inducing infertility, and then to construct synthetic peptides containing these determinants. Possessing the capability for synthesizing a molecule with such properties makes the immunological approach to fertility control feasible". *Karolinska Symposia on Research Methods in Reproductive Endocrinology* 7th Symposium: Immunological Approaches to Fertility Control, Geneva, 1974, 202-222.

Subsequent investigations by Dr. Goldberg and his research associates identified several amino acid sequences of mouse LDH-C$_4$ which in isolated form (e.g., as short chain peptides) bind to LDH-C$_4$ antiserum. Wheat, et al. (1981) in Rich, et al., *Peptides: Synthesis-Structure-Function, Proc. 7th Amer. Peptide Symp.*, pp. 557-560; and Gonzales-Prevatt, et al. (1982), *Mol. Immunol.* 19:1579-1585. Antigenic peptide compounds based on these sequences have been patented. See U.S. Pat. Nos. 4,290,944; 4,310,456; 4,353,822; 4,377,516, 4,392,997; 4,578,219; and 4,585,587.

These antigenic peptides are useful in preparing vaccines to reduce female fertility. Immunization of female mammals results in the development of circulating antibodies specific to LDH-C$_4$. These immunoglobulins reach the female reproductive tract as a transudate of serum. Kille, et al. (1977), *Biol. Reprod.* 20:863-871. Antibody in cervical mucus, uterine fluids, and oviducal fluids combine with LDH-C$_4$ on the sperm surface and impede the progress of the male gamete, presumably by agglutination. Systemic immunization with LDH-C$_4$ markedly interferes with sperm transport in the female reproductive tract. Kille et al. (1980), *J. Reprod. Immunol.* 2:15-21.

The current status of research on LDH-C$_4$ and antigenic peptides for use in female contraceptive vaccines is summarized in two recent publications by the Goldberg group: Goldberg, et al. (1983) *In Immunology of Reproduction*, Chapt. 22, pp. 493-504; and Wheat, et al. (1983), in *Isozymes: Current Topics in Biological and Medical Research*, Vol. 7, pp. 113-140.

In the prior work on synthetic antigenic peptides corresponding to antigenic regions of LDH-C$_4$, it was assumed that the antigenic regions of mouse LDH-C$_4$ enzyme were essentially homologous with those of human LDH-C$_4$. Tests in female rabbits had demonstrated immunization effects from the mouse antigenic sequences. The synthetic peptide corresponding to the mouse LDH-C$_4$ sequence 5-15 was found to be antigenic for immunizing not only female rabbits but also female baboons. See Goldberg and Shelton, in "Immunological Approaches to Contraception and Promotion of Fertility", pages 219-230 (ed. G. P. Talwar, Plenum Publishing Corp., 1986).

SUMMARY OF INVENTION

This invention is based in part on the discovery that certain of the antigenic sequences of mouse LDH-C$_4$ are not homologous to the corresponding sequences of human LDH-C$_4$ but rather vary markedly in their amino acid content. The peptides of this invention correspond exactly with human LDH-C$_4$ antigenic regions and thereby differentiate the prior antigenic peptides. The synthetic peptides of this invention are thereby expressly adapted for producing antibodies binding to the lactate dehydrogenase enzyme of human semen. It is believed that these peptide compounds of this invention will have greater effectiveness in vaccines for reducing the fertility of women.

DETAILED DESCRIPTION

In the following description, standard amino acid names and abbreviations are used, as set out in the following table.

| Names and Abbreviations of Amino Acids | |
|---|---|
| Amino Acids | Three-letter Abbreviations |
| alanine | Ala |
| arginine | Arg |
| asparagine | Asn |
| aspartic acid | Asp |
| cysteine | Cys |
| glutamine | Gln |
| glutamic acid | Glu |
| glycine | Gly |
| histidine | His |
| isoleucine | Ile |
| leucine | Leu |
| lysine | Lys |
| methionine | Met |
| phenylalanine | Phe |
| proline | Pro |
| serine | Ser |
| threonine | Thr |
| tryptophan | Trp |
| tyrosine | Tyr |
| valine | Val |

Synthetic peptide compounds of the present invention, which comprise a class of antigenic peptides that are capable of producing antibodies binding to the lactate dehydrogenase enzyme of human semen (LDH-C4), are represented by the following N-terminal to C-terminal sequences:

```
    5              9  10                                  (1)
Glu—Gln—Leu—Ile—Glu—Lys—
                (Gln) (Asn)

12    13   14a  14b  15
            —Leu—Ile——Glu—Asp—Asp—Glu
                (Val) (Pro) (Glu)      (Lys)

211     213       214 215                               (2)
Thr—Leu—Asp—Pro—Lys—Leu—Gly—Thr—
 (Ser)    (Asn)    (Ala)(Ile)

226
            —Asp—Ser—Asp—Lys—Glu—His—Trp—Lys 231    233  234 235  236                                 (3)
Gln—Val—Ile——Gln—Ser——Ala—Tyr—
        (Val)(Glu)(Gly)  (Gly)

239  240   241    242 243
                    —Glu—Ile——Ile——Lys——Leu—Lys
                         (Val) (Leu) (Asn)   (Met)

283     285                                              (4)
Glu—Glu—Leu—Phe—Leu—Ser—Ile—
         (Val)

295  296
            —Pro—Cys—Val—Leu—Gly—Arg—Asn—
                              (Glu) (Ser)

298  299      301      303
                    —Gly—Val—Ser—Asp—Val—Val—Lys
                        (Ile)(Thr)    (Phe)

304    306  307 308                                      (5)
Ile—Asn—Leu——Asn—Ser—Glu—Glu—
 (Val) (Met)  (Thr)(Ala)

312       314     316
                    —Glu—Ala—Leu—Phe—Lys—Lys
                         (Gly)      (Leu)

324                  329 330                            (6)
Ile—Gln—Lys—Asp—Leu—Ile——Phe
(Met)                  (Glu)(Leu)
```

The amino acids of the above peptides are all L-amino acids with the exception of glycine which does not have L-D forms. The numbers shown above the amino acids correspond to the numbering system previously used for amino acids of mouse LDH-C4, See Wheat and Goldberg (1985), *Annals N.Y. Acad. Sci*, 438:156–169. Mouse LDH-C4 was numbered 1 to 330 with the insertion of aspartic acid treated as follows: Pro-13, Glu-14a, Asp-14b, Lys-15, etc.

The amino acids indicated in parentheses under certain of the amino acids of peptides 1 to 6 represent the different amino acids of the corresponding sequences of mouse LDH-C4. With reference to peptide (1), amino acids 9, 10, 12, 13, 14a and 15 are different in the human LDH-C4 than in mouse LDH-C4. Similar differences are shown with respect to each of the peptide compounds, peptide (2) having four different amino acids, peptide (3) having eight different amino acids, peptide (4) having six different amino acids, peptide (5) having six different amino acids, and peptide (6) having three different amino acids.

Peptide (1) can be extended at its N-terminal end by 1 to 5 amino acids corresponding to amino acids 1 to 5 of the LDH-C4 human enzyme. Peptide (1) can therefore be produced and used in five different forms, as represented by the following:

(1 a) Glu-Gln-Leu-Ile-Glu-Lys-Leu-Ile-Glu-Asp-Asp-Glu;

(1 b) Lys-Glu-Gln-Leu-Ile-Glu-Lys-Leu-Ile-Glu-Asp-Asp-Glu;

(1 c) Val-Lys-Glu-Gln-Leu-Ile-Glu-Lys-Leu-Ile-Glu-Asp-Asp-Glu;

(1 d) Thr-Val-Lys-Glu-Gln-Leu-Ile-Glu-Lys-Leu-Ile-Glu-Asp-Asp-Glu; and (1 e) Ser-Thr-Val-Lys-Glu-Gln-Leu-Ile-Glu-Lys-Leu-Ile-Glu-Asp-Asp-Glu.

All the above sequences extend from N-terminal to C-terminal ends of the peptides, and all of the amino acids with the exception of glycine are in their L-forms.

In synthesizing the peptides of this invention, it is sometimes convenient to add cysteine (Cys) at the N-terminal end. When this is done, the sequences are extended by an N-terminal Cys. It should be understood that any of the peptide compounds can be produced and used in that form. This permits conjugation of the peptide to a carrier for immunization.

The peptide compounds of the present invention can be synthesized from their constituent amino acids. For example, the synthesis can be carried out by the Merrifield solid phase method, as described in *J.A.C.S.* 85:2149–2154 (1963). This solid phase method for synthesizing sequences of amino acids is also described in Stewart and Young, *Solid Phase Peptide Synthesis* (W. H. Freeman and Co., San Francisco, 1969), pages 1–4. In this procedure, the C-terminal amino acid is attached to chloromethylated polystyrene-divinylbenzene copolymer beads. Each subsequent amino acid, with suitable protecting group, is then added sequentially to the growing chain. For example, as described in the Merrifield article, the protective group may be a carbobenzoxy group. By the procedure of coupling, deprotection, and coupling of the next amino acid, the desired amino acid sequence and chain length can be produced. As a final step, the protective group is removed from the N-terminal amino acid (viz., lysine and the C-terminal amino acid is cleaved from the resin, using a suitable reagent, such as trifluoroacetic acid and hydrogen bromide. Since this synthesis procedure is well known, it is not believed that it will be necessary to further describe it herein.

To utilize the antigenic peptides of this invention in the form of a fertility reducing vaccine, the peptide is conjugated to a carrier molecule, which is preferably a protein which itself elicits an antigenic response and which can be safely administered. For example, the peptide can be coupled to tetanus toxoid for administration by intramuscular injection. For example, a mixture of 1 μMole tetanus toxoid, 60 μMoles antigenic peptide, and 18 millimoles 1-ethyl-3-(3 dimethyl aminopropyl) carbodiimide hydrochloride reacted in water (pH6) for 12 hours at room temperature and 24 hours at 4° gives a product containing 3.5 moles of peptide/mole tetanus toxoid. Excess reactants can be removed by dialysis or gel filtration. See Pique et al., *Immunochemistry* 15:55–60 (1978). Alternatively, the peptide may be coupled using bisadiazotized benzidine (Bassiri et al., *Endocrinology*, 90–722 (1972)) or glutaraldehyde.

Peptides can be made immunogenic by adding a fatty acid (lauric acid) or a short series of hydrophobic amino acids (Phe-Leu-Leu-Val-Val-Cys-Tyr-Gly-Gly) to one end of the peptides and hydrophobically binding that end to meningococcal outer membrane proteins (Smith et al., 6th Int'l Congress of Immunol. Abst., p. 248, 1986; Lowell, G., personal communication to E.G., 1986).

For intramuscular injection, the coupled peptides may be suspended in a sterile isotonic saline solution or other conventional vehicle, and, if desired, an adjuvant may be included. A preferred use of such a vaccine is for administration to human females. Antibodies will be formed which will appear in the oviduct fluids and thereby produce a significant reduction in fertility. For this purpose, the amount to be administered will range from about 1 to 10 milligrams (mg) of the antigenic peptide.

The scientific basis of the present invention as well as its practical application are more fully illustrated by the following experimental examples.

EXPERIMENTAL EXAMPLES

EXAMPLE I

A human testis specimen was obtained after coadjuvant orchiectomy during operation of a prostatic cancer. RNA was extracted from the testis by the guanidinium isothiocyanate procedure followed by CsCl centrifugation, and total polyadenylated RNA was selected by oligo dT-cellulose. A cDNA expression library was constructed in λgt11 following a procedure previously reported for the generation of a human placental library (Millan (1986), *J. Biol. Chem.*, 251:3112–3115. cDNA larger than 1.0 kb was ligated to λgt11 arms. The recombinant DNA was packaged using the Gigapack System (Vector Cloning Systems, San Diego, Calif.). Recombinant phages were obtained at an efficiency of 35,000 plaques/ng of double-stranded cDNA. The library, consisting of $1.8 \times 10^6$ independent recombinant phages and containing less than 5% nonrecombinants, was amplified on *E. coli* Y1088.

Immunochemical screening

Three high titer rabbit sera produced by immunization with purified mouse LDH-$C_4$ protein were pooled and used to screen the human testis cDNA expression library. The antiserum was diluted 100-fold and absorbed with a lysate of *E. coli* strain Y1090. The testis λgt11 library was plated at a density of $2.5 \times 10^4$ plaque-forming units (pfu) per 150 mm$^3$ petri dish with *E. coli* Y1090 as host bacteria. After growth at 42° C. and induction with IPTG, the nitrocellulose filters were screened and bound antibody detected by use of goat anti-rabbit IgG coupled to horseradish peroxidase. The generation of murine monoclonal antibodies against mouse LDH-$C_4$ has previously been reported. Goldman-Leiken and Goldberg (1983), *Proc. Nat'l. Acad. Sci. USA* 74:5463–5467. Monoclonal antibody $F_6H_8$ (an IgG$_{2a}$, κ) was used in a secondary screening and binding was detected with goat antimouse IgG labeled with horseradish peroxidase.

Sequence Analysis cDNA inserts were subcloned into the Eco R1 site of M13mp19 and sequenced using the universal 17-mer sequencing primer (P-L Biochemicals) and 17- and 18-mer oligonucleotides synthesized on an Applied Biosystems DNA synthesizer. Sequencing of the clones was accomplished by the Sanger dideoxy chain termination procedure using the Klenow fragment of DHA polymerase and $^{35}$SdATP as tracer. See Sanger et al., *Proc. Nat'l. Acad. Sci. USA*, 74:5463–5467; and Biggen et al. (1983), *Proc. Nat'l. Acad. Sci. U.S.A.*, 80:3963–3965.

The pooled antisera prepared as described above reacted with 12 putative clones upon screening $1.8 \times 10^5$ pfu from the expression library. The positive clones were isolated as single plaques and rescreened as macroplaques. Three of these twelve putative clones tested positive with the $F_6H_8$ monoclonal antibody to mouse LDH-$C_4$. These three clones contained inserts 0.8, 0.9 and 1.0 kbp long that cross-hybridized with each other in Southern blotting. The clone selected for sequence analysis contained a noncross-hybridizing fragment of 0.6 kbp in addition to the 1.0 kbp cDNA suggesting an internal EcoRI restriction site in the LDH-$C_4$ cDNA. In Northern blot analysis, the nick-translated 1.0 kb subfragment detected a single mRNA species of approximately 1.5 kb in human testis RNA but not in placental RNA. The determined sequence of the human LDH-$C_4$ cDNA is shown in Diagram A. The complete cloned cDNA included the flanking regions illustrated in diagrams B and C. The 1.0 kbp subfragment includes 66 bp of 5' flanking region and encodes most of the LDH-$C_4$ protein. The 0.6 kbp subfragment codes for the last 24 amino acids of LDH-$C_4$, a flanking region and a poly A tail.

DIAGRAM A cDNA and Corresponding Amino Acid Sequences for Human LDH-$C_4$ Enzyme[1]

```
5'-CGCCTCAACTGTCGTTGGTGTATTTTTCTGGTGTCACTTCTGTGCCTTCCTTCAAAGGTTCTCCAA ATG TCA ACT    75
                                                                     Ser Thr    2

GTC AAG GAG CAG CTA ATT GAG AAG CTA ATT GAG GAT GAT GAA AAC TCC CAG TGT AAA ATT ACT  138
Val Lys  Glu Gln Leu Ile Glu Lys Leu Ile Glu Asp Asp Glu  Asn Ser Gln Cys Lys Ile Thr  23
     5                                    14a 14b 15

ATT GTT GGA ACT GGT GCC GTA GGC ATG GCT TGT GCT ATT AGT ATC TTA CTG AAG GAT TTG GCT  201
Ile Val Gly Thr Gly Ala Val Gly Met Ala Cys Ala Ile Ser Ile Leu Leu Lys Asp Leu Ala   44

GAT GAA CTT GCC CTT GTT GAT GTT GCA TTG GAC AAA CTG AAG GGA GAA ATG ATG GAT CTT CAG  264
Asp Glu Leu Ala Leu Val Asp Val Ala Leu Asp Lys Leu Lys Gly Glu Met Met Asp Leu Gln   65

CAT GGC AGT CTT TTC TTT AGT ACT TCA AAG GTT ACT TCT GGA AAA GAT TAC AGT GTA TCT GCA  327
His Gly Ser Leu Phe Phe Ser Thr Ser Lys Val Thr Ser Gly Lys Asp Tyr Ser Val Ser Ala   86

AAC TCC AGA ATA GTT ATT GTC ACA GCA GGT GCA AGG CAG CAG GAG GGA GAA ACT CGC CTT GCC  390
Asn Ser Arg Ile Val Ile Val Thr Ala Gly Ala Arg Gln Gln Glu Gly Glu Thr Arg Leu Ala  107

CTG GTC CAA CGT AAT GTG GCT ATA ATG AAA ATA ATC ATT CCT GCC ATA GTC CAT TAT AGT CCT  453
Leu Val Gln Arg Asn Val Ala Ile Met Lys Ile Ile Ile Pro Ala Ile Val His Tyr Ser Pro  128
```

DIAGRAM A-continued cDNA and Corresponding Amino Acid Sequences for Human LDH-C₄ Enzyme[1]

```
GAT TGT AAA ATT CTT GTT GTT TCA AAT CCA GTG GAT ATT TTG ACA TAT ATA GTC TGG AAG ATA      516
Asp Cys Lys Ile Leu Val Val Ser Asn Pro Val Asp Ile Leu Thr Tyr Ile Val Trp Lys Ile      149

AGT GGC TTA CCT GTA ACT CGT GTA ATT GGA AGT GGT TGT AAT CTA GAC TCT GCC CGT TTC CGT      579
Ser Gly Leu Pro Val Thr Arg Val Ile Gly Ser Gly Cys Asn Leu Asp Ser Ala Arg Phe Arg      170

TAC CTA ATT GGA GAA AAG TTG GGT GTC CAC CCC ACA AGC TGC CAT GGT TGG ATT ATT GGA GAA      642
Tyr Leu Ile Gly Glu Lys Leu Gly Val His Pro Thr Ser Cys His Gly Trp Ile Ile Gly Glu      191

CAT GGT GAT TCT AGT GTG CCC TTA TGG AGT GGG GTG AAT GTT GCT GGT GTT GCT CTG AAG ACT      705
His Gly Asp Ser Ser Val Pro Leu Trp Ser Gly Val Asn Val Ala Gly Val Ala Leu Lys |Thr     212
                                                                                  211

CTG GAC CCT AAA TTA GGA ACG GAT TCA GAT AAG GAA CAC TGG AAA AAT ATC CAT AAA CAA GTT      768
 Leu Asp Pro Lys Leu Gly Thr Asp Ser Asp Lys Glu His Trp Lys |Asn Ile His Lys |Gln Val   233
                                                     226              231

ATT CAA AGT GCC TAT GAA ATT ATC AAG CTG AAG GGG TAT ACC TCT TGG GCT ATT GGA CTG TCT      831
 Ile Gln Ser Ala Tyr Glu Ile Ile Lys Leu Lys| Gly Tyr Thr Ser Trp Ala Ile Gly Leu Ser    254
                                       243

GTG ATG GAT CTG GTA CCT TTG AAA AAT CTT AGG AGA GTG CAC CCA GTT TCC ACC ATG GTT AAG      894
Val Met Asp Leu Val Pro Leu Lys Asn Leu Arg Arg Val His Pro Val Ser Thr Met Val Lys      275

GGA TTA TAT GGA ATA AAA GAA GAA CTC TTT CTC AGT ATC CCT TGT GTC TTG GGG CGG AAT GGT      957
Gly Leu Tyr Gly ILe Lys |Glu Glu Leu Phe Leu Ser Ile Pro Cys Val Leu Gly Arg Asn Gly     296
                  283

GTC TCA GAT GTT GTG AAA ATT AAC TTG AAT TCT GAG GAG GAG GCC CTT TTC AAG AAG AGT GCA     1020
Val Ser Asp Val Val Lys ||Ile Asn Leu Asn Ser Glu Glu Glu Ala Leu Phe Lys Lys| Ser Ala   317
                  303   304                                              316

GAA ACA CTT TGG AAT ATT CAA AAG GAT CTA ATA TTT TAA ATTAAAGCCTTCTAATGTTCCACTGTTTGGA     1090
Glu Thr Leu Trp Asn |Ile Gln Lys Asp Leu Ile Phe|                                         329
                      324                 330

GAACAGAAGATAGCAGGCTGTGTATTTTAAATTTTGAAAGTATTTTCATTGATCTTAAAAAATAAAAACAAATT             1173
GGAGACCTGAAAAAAAAAAAAAAAA-3'                                                             1189
```

[1] Human chemical sequence numbers are in right-hand column, with corresponding mouse sequence numbers at each end of bracketed antigenic sequences.

EXAMPLE II

Synthesis of the peptides Cys-Ser-Thr-Val-Lys-Glu-Gln-Leu-Ile-Glu-Lys-Leu-Ile-Glu-Asp-Asp-Glu, and Cys-Glu-Gln-Leu-Ile-Glu-Lys-Leu-Ile-Glu-Asp-Asp-Glu was carried out employing known solid phase techniques. In a preferred procedure Fmoc protected Glu, representing the -COOH terminal group of the above peptides, was coupled to 1) p-alkoxybenzyl alcohol resin and 2) dimethylacrylamide-ethylene bisacrylamide-acrylsarcosine methyl ester copolymer that has been derivatised with ethylene diamine and functionalized with a linkage agent. The coupling or esterification reaction was carried out in the presence of dimethylaminopyridine. The amino protecting group was then selectively removed utilizing a suitable reagent whose nature will depend on the protecting groups. In the preferred embodiment the fluorenylmethoxycarbonyl (Fmoc) group was utilized for amino group protection and 20% piperidine in dimethylformamide was the selective deprotection agent. After deprotection, the glutamine is treated with protected aspartic acid, preferably Fmoc-Asp-tbutyl ester which has been preactivated with dicyclohexyl-carbodiimide as the symmetrical anhydride in a manner known per se as to form a peptide bond between the free amino group of the glutamine and the carboxyl group of protected aspartic acid. A double coupling procedure was carried out to ensure 100% completion of reaction. The cycle of deprotection and coupling with amino acid derivatives that has been preformed as the symmetric anhydride or pentafluorophenyl ester was then repeated with the remaining amino-acids in the sequence order of the above peptide. Some of the amino acids required sidechain blocking groups besides the alpha-amino protection. Such amino acids and the blocking groups are as follows:

Asp (t-butyl), Lys (ε-Boc), Glu (t-butyl), Ser (O-t-butyl), Thr (Ot-butyl), Cys (N-tBoc) where BOC is t-butyloxycarbonyl, S-S-Et (Sethylthio). Completion of the synthesis provided the following peptide resin

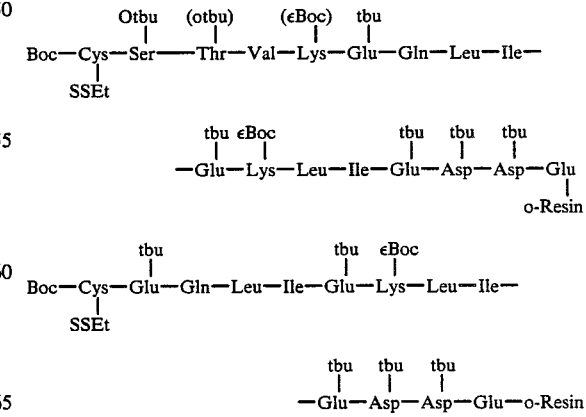

Decoupling of the peptide from the resin was accomplished by treatment with 60% trifluoroacetic acid/40% dichloromethane containing 10% anisole with concomittant cleavage of all protecting groups to produce the desired peptide, identified as above. The S-SEt protecting group was removed by treatment with a reducing agent such as Dithiothreitol.

EXAMPLE III

Two rabbits were injected with the peptide of Example 1a and with the peptide of Example 1e. Both peptides were conjugated to diphtheria toxoid as carrier protein. Antisera from each of these immunized animals showed a positive antibody response to the non-conjugated peptides within two weeks of the primary immunization. Therefore, we conclude that these preparations are antigenic. Furthermore, analyses by gel electrophoresis of antibody binding in human sperm extracts revealed a specific reaction with LDH-$C_4$. This methodology is described in GoldmanLeikin and Goldberg (1983), *Proc. Nat'l. Acad. Sci. USA* 80, 3774–3778.

We claim:

1. A synthetic peptide compound capable of producing antibodies binding to the lactate dehydrogenase enzyme of human semen (LDH-$C_4$), consisting of a peptide selected from the group of peptides represented by the following N-terminal to C-terminal amino acid sequences:

(1 a) Glu-Gln-Leu-Ile-Glu-Lys-Leu-Ile-Glu-Asp-Asp-Glu;

(1 b) Lys-Glu-Gln-Leu-Ile-Glu-Lys-Leu-Ile-Glu-Asp-Asp-Glu;

(1 c) Val-Lys-Glu-Gln-Leu-Ile-Glu-Lys-Leu-Ile-Glu-Asp-Asp-Glu;

(1 d) Thr-Val-Lys-Glu-Gln-Leu-Ile-Glu-Lys-Leu-Ile-Glu-Asp-Asp-Glu;

(1 e) Ser-Thr-Val-Lys-Glu-Gln-Leu-Ile-Glu-Lys-Leu-Ile-Glu-Asp-Asp-Glu;

(2) Thr-Leu-Asp-Pro-Lys-Leu-Gly-Thr-Asp-Ser-Asp-Lys-Glu-His-Trp-Lys;

(3) Gln-Val-Ile-Gln-Ser-Ala-Tyr-Glu-Ile-Ile-Lys-Leu-Lys;

(4) Glu-Glu-Leu-Phe-Leu-Ser-Ile-Pro-Cys-Val-Leu-Gly-Arg-Asn-Gly-Val-Ser-Asp-Val-Val-Lys;

(5) Ile-Asn-Leu-Asn-Ser-Glu-Glu-Glu-Ala-Leu-Phe-Lys-Lys; and (6) Ile-Gln-Lys-Asp-Leu-Ile-Phe wherein Gly represents glycine and Ala, Arg, Asn, Asp, Cys, Gln, Glu, His, Ile, Leu, Lys, Met, Phe, Pro, Ser, Thr, Trp, Tyr, and Val respectively represent the L-amino acid forms of alanine, arginine, asparagine, aspartic acid, cysteine, glutamine, glutamic acid, histidine, isoleucine, leucine, lysine, methionine, phenylalanine, proline, serine, threonine, tryptophan, tyrosine and valine, and wherein Cys is either present or not present as an additional amino acid at the N-terminal end of the peptide compound.

2. A synthetic peptide compound of claim 1 having an amino acid sequence selected from sequences (1a) to (1e).

3. A synthetic peptide compound of claim 1 having the amino acid sequence (2).

4. A synthetic peptide compound of claim 1 having the amino acid sequence (3).

5. A synthetic peptide compound of claim 1 having the amino acid sequence (4).

6. A synthetic peptide compound of claim 1 having the amino acid sequence (5).

7. A synthetic peptide compound of claim 1 having the amino acid sequence (6).

* * * * *